US009003645B1

(12) United States Patent
Yost et al.

(10) Patent No.: US 9,003,645 B1
(45) Date of Patent: Apr. 14, 2015

(54) ULTRASONIC DEVICE FOR ASSESSING THE QUALITY OF A WIRE CRIMP

(71) Applicant: The United States of America as represented by the Administrator of the National Aeronautics and Space Administration, Washington, DC (US)

(72) Inventors: William T. Yost, Newport News, VA (US); Daniel F. Perey, Yorktown, VA (US); Karl E. Cramer, Yorktown, VA (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 262 days.

(21) Appl. No.: 13/743,750

(22) Filed: Jan. 17, 2013

(51) Int. Cl.
  B23P 19/00 (2006.01)
  H01R 43/042 (2006.01)
  H01R 43/048 (2006.01)

(52) U.S. Cl.
  CPC .................................... H01R 43/048 (2013.01)

(58) Field of Classification Search
  CPC ................. A61B 2019/2269; Y10T 29/49169; G01N 29/2456
  USPC ............. 29/753, 593, 595, 705, 720; 72/17.2, 72/20.1, 21.4, 31.01, 416
  See application file for complete search history.

(56) References Cited

U.S. PATENT DOCUMENTS

| 698,241 | A | 4/1902 | Bailey |
| 3,157,075 | A | 11/1964 | Filia |
| 3,292,413 | A | 12/1966 | Falcioni |
| 4,062,227 | A | 12/1977 | Heyman |
| 4,373,394 | A | 2/1983 | Renzel et al. |
| 4,385,515 | A | 5/1983 | Link et al. |
| 5,046,241 | A | 9/1991 | Ricard |
| 5,092,026 | A | 3/1992 | Klemmer et al. |
| 5,197,186 | A | 3/1993 | Strong et al. |
| 5,297,435 | A | 3/1994 | Papazian |
| 5,814,728 | A | 9/1998 | Okawa et al. |
| 5,937,505 | A * | 8/1999 | Strong et al. ............... 29/593 |
| 6,196,062 | B1 | 3/2001 | Wright et al. |
| 6,393,924 | B1 | 5/2002 | Eder et al. |

(Continued)

OTHER PUBLICATIONS

Cheng-Hsun, et al., "Ultrasonic Evaluation of Temper-Embrittlement for Martensitic Stainless Steel," Jun. 20, 2003, pp. 2363-2368, vol. 44, No. 11.

(Continued)

*Primary Examiner* — Thiem Phan
(74) *Attorney, Agent, or Firm* — Andrea Z. Warmbier

(57) ABSTRACT

A system for determining the quality of an electrical wire crimp between a wire and ferrule includes an ultrasonically equipped crimp tool (UECT) configured to transmit an ultrasonic acoustic wave through a wire and ferrule, and a signal processor in communication with the UECT. The signal processor includes a signal transmitting module configured to transmit the ultrasonic acoustic wave via an ultrasonic transducer, signal receiving module configured to receive the ultrasonic acoustic wave after it passes through the wire and ferrule, and a signal analysis module configured to identify signal differences between the ultrasonic waves. The signal analysis module is then configured to compare the signal differences attributable to the wire crimp to a baseline, and to provide an output signal if the signal differences deviate from the baseline.

19 Claims, 4 Drawing Sheets

(56) References Cited

U.S. PATENT DOCUMENTS

| | | | |
|---|---|---|---|
| 6,418,769 | B1 | 7/2002 | Schreiner |
| 6,553,803 | B1 | 4/2003 | Heingartner et al. |
| 7,124,608 | B2 * | 10/2006 | Goop .......................... 72/21.3 |
| 7,181,942 | B2 | 2/2007 | Yost et al. |
| 2004/0027578 | A1 | 2/2004 | Drake, Jr. et al. |
| 2004/0055354 | A1 | 3/2004 | Anton |
| 2005/0193792 | A1 | 9/2005 | Yost et al. |
| 2008/0276678 | A1 | 11/2008 | Pacaud et al. |
| 2009/0314087 | A1 | 12/2009 | Ales et al. |
| 2012/0192407 | A1 | 8/2012 | Yost et al. |

OTHER PUBLICATIONS

PCT International Search Report, PCT/US2012/023423, May 16, 2012.

* cited by examiner

ULTRASONIC DEVICE FOR ASSESSING THE QUALITY OF A WIRE CRIMP

STATEMENT REGARDING FEDERALLY SPONSORED RESEARCH OR DEVELOPMENT

The invention described herein was made by employees of the United States Government and may be manufactured and used by or for the Government for governmental purposes without payment of any royalties thereon or therefor.

TECHNICAL FIELD

The present invention relates to a device for assessing the connectivity between a wire and a crimp connector.

BACKGROUND OF THE INVENTION

Crimping is a cold-working process used to join mutually-deformable objects, at least one of which is typically constructed of metal or another malleable material. For example, in forming a crimped electrical connection, a wire may be deformed with respect to a barrel or a ferrule in order to form a crimped joint, hereinafter referred to as a crimp for simplicity. Crimping tools are used to mechanically join a ferrule to a wire. An improperly crimped ferrule/wire connection may contain loose wires, and the deformation of the ferrule may provide an inadequate clamping force.

Conventional quality testing of a pull-out force of a crimp is performed manually. That is, the crimp, along with any settings of the particular tool used to form the crimp, are evaluated via the pull force required to separate the crimped ferrule from the wire or bundled wires therein. Once the crimps are determined to support a threshold minimum load, usually set on the basis of wire gauge and crimp ferrule qualities, the crimping tool is placed in service. However, conventional pull testing may inadequately measure transport across the crimps, and therefore such pull test results are not closely linked with electrical conduction properties of the resultant crimp.

Measures of the quality of the electrical conduction across a crimp may be derived from the ability to transmit ultrasonic energy across the ferrule—wire interface, since electrical and ultrasonic transmission are both fundamentally related to the asperity density at the wire-ferrule interface. One method of ultrasonically analyzing a crimp is described in U.S. Pat. No. 7,181,942 to Yost et al., the contents of which are hereby incorporated by reference in their entirety.

SUMMARY OF THE INVENTION

A system for determining the quality of an electrical wire crimp between a wire and ferrule includes an ultrasonically equipped crimp tool (UECT) configured to transmit an ultrasonic wave through a wire and ferrule which is received by a second ultrasonic piezoelectric transducer whose output is sent to a signal processor. The UECT may include a first ultrasonic transducer configured to generate an ultrasonic wave in response to a first analog electrical signal, and a second ultrasonic transducer configured to oppose the first ultrasonic transducer and configured to generate a second analog electrical signal in response to a sensed ultrasonic wave.

The signal processor may be in communication with the UECT and with each of the respective first and second ultrasonic transducers, and may include a signal transmitting module, a signal receiving module, and a signal analysis module. The signal transmitting module may be configured to transmit the first analog electrical signal to the first ultrasonic transducer, where the first analog electrical signal has frequencies within the ultrasonic transducer's frequency range. The signal receiving module configured to receive the second analog electrical signal from the second ultrasonic transducer.

The signal analysis module of the signal processor may be configured to identify signal differences between the first and second analog electrical signals, and particularly those that are attributable to the wire crimp. Additionally, the signal analysis module may compare the signal differences attributable to the wire crimp to a baseline, and provide an output signal if the signal differences substantially deviate from the baseline.

In an embodiment, the signal differences identified by the signal analysis module may include an attenuation of the signal amplitude of the second analog electrical signal relative to the first analog electrical signal. Additionally, they may include a shift of the phase of the second analog electrical signal relative to the first analog electrical signal and/or include the existence of harmonic content ultrasonically generated within the wire-ferrule complex and detected within the second ultrasonic transducer where it is converted into an analog electrical signal.

The signal processor may further include non-volatile memory, and may store the baseline in the non-volatile memory. The baseline may be representative of the signal differences expected from a characteristic crimp derived from a statistical average of a sample of crimps. Alternatively, the baseline may be obtained from test data of the electrical wire crimp during a previous test.

The UECT may further include a first compression element and a second compression element configured to contact the ferrule on substantially opposing sides of the ferrule. The first transducer may be coupled with the first compression element, and the second transducer may be coupled with the second compression element. In an embodiment, each of the first and second compression elements may include a contact-promoting material disposed on a portion of the respective element that is configured to contact the ferrule. The contact-promoting material may have an adhesive quality that further aids in promoting adequate, ultrasonic-transmitting contact.

The system may further include a third ultrasonic transducer in communication with the wire and configured to generate a third analog electrical signal in response to a sensed shear ultrasonic acoustic wave. The signal processor may be configured to receive the third analog electrical signal from the third ultrasonic transducer, and the signal analysis module is further configured to identify signal differences between the first and third analog electrical signals that are attributable to the wire crimp.

The above features and advantages and other features and advantages of the present invention are readily apparent from the following detailed description of the best modes for carrying out the invention when taken in connection with the accompanying drawings.

DETAILED DESCRIPTION OF THE INVENTION

Figure 1:
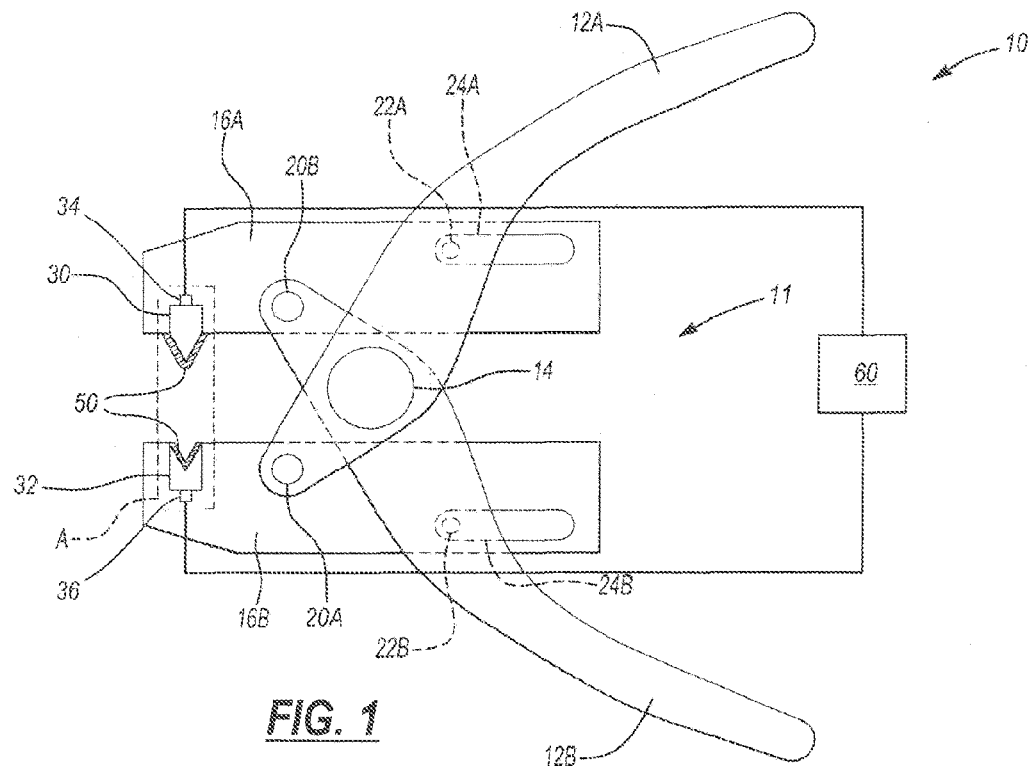
FIG. 1 is a schematic side view illustration of an ultrasonically equipped crimp tool (UECT) in an uncompressed position.
Figure 2:
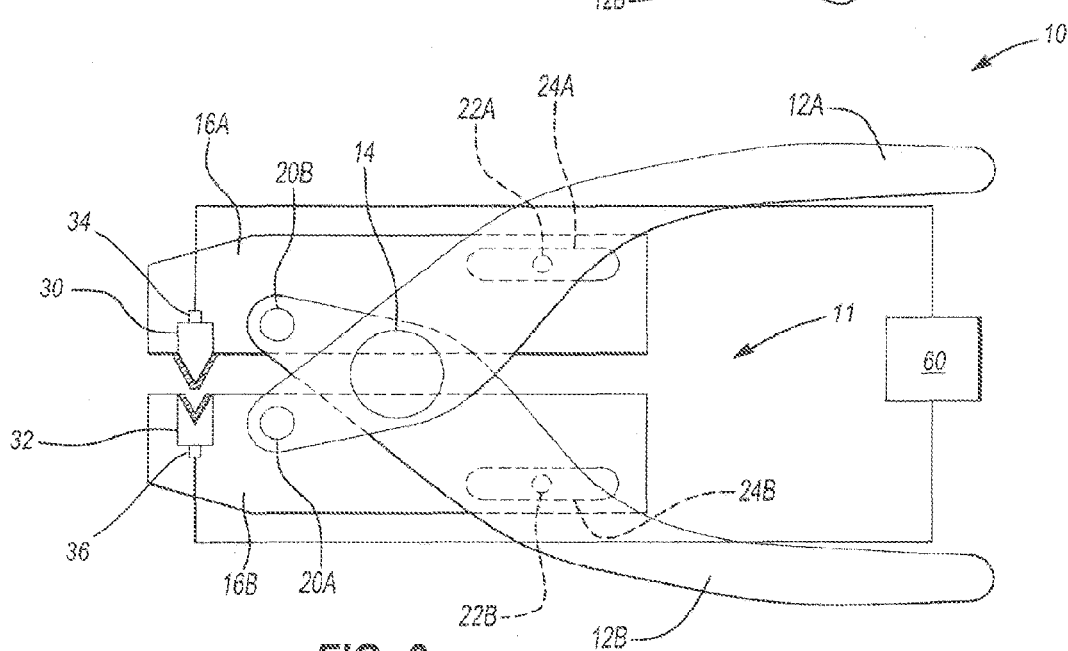
FIG. 2 is a schematic side view illustration of the UECT of FIG. 1, with the UECT in a compressed position.

Referring to the drawings wherein like reference numbers represent like components throughout the several figures, FIGS. 1 and 2 show a system 10 that may be used to evaluate or re-evaluate the quality of an electrical crimp. As illustrated, the system 10 may include an ultrasonically equipped crimp tool ("UECT") 11 in communication with a signal processor 60. The UECT 11 may be used to forcibly compress a ferrule or other deformable crimping element about a wire for the purpose of creating a firm mechanical and electrical coupling. FIG. 1 generally illustrates a UECT 11 in an open or uncompressed state, and FIG. 2 generally illustrates the UECT 11 in a closed or compressed state.

The UECT 11 may include a pair of handles 12A and 12B which may each be connected to, and allowed to rotate about, a coaxial pivot 14. The UECT 11 may also include jaws 16A and 16B positioned opposite one another, where handle 12A is pivotally attached to the jaw 16B at a pivot 20A, and handle 12B is pivotally attached to jaw 16A at a pivot 20B. Guide pins 22A and 22B may be secured on the respective handles 12A and 12B, and may be each be adapted to ride within an elongated slot 24A, 24B provided in the respective jaws 16A, 16B.

Closure of the handles 12A and 12B, best shown in FIG. 2, may cause the handles to rotate about the coaxial pivot 14, and may result in a closure of the jaws 16A and 16B relative to each other. The pivot mounting of the jaws 16A, 16B on the handles 12A, 12B and cooperation of guide pins 22A, 22B with respective slots 24A and 24B may cause the jaws 16A, 16B to maintain orientation with respect to one another.

Each of the jaws 16A, 16B may support a respective compression element, such as, for example, a punch 30 and an anvil 32 (hereinafter referred to only as compression elements 30, 32), which may be configured to compress a deformable, tubular ferrule onto a more centrally disposed wire. It should be understood that other suitably shaped compression elements may be used, and, for example, may include any combination of convex, concave, or other shaped surface designs to optimize operation.

Figure 3:
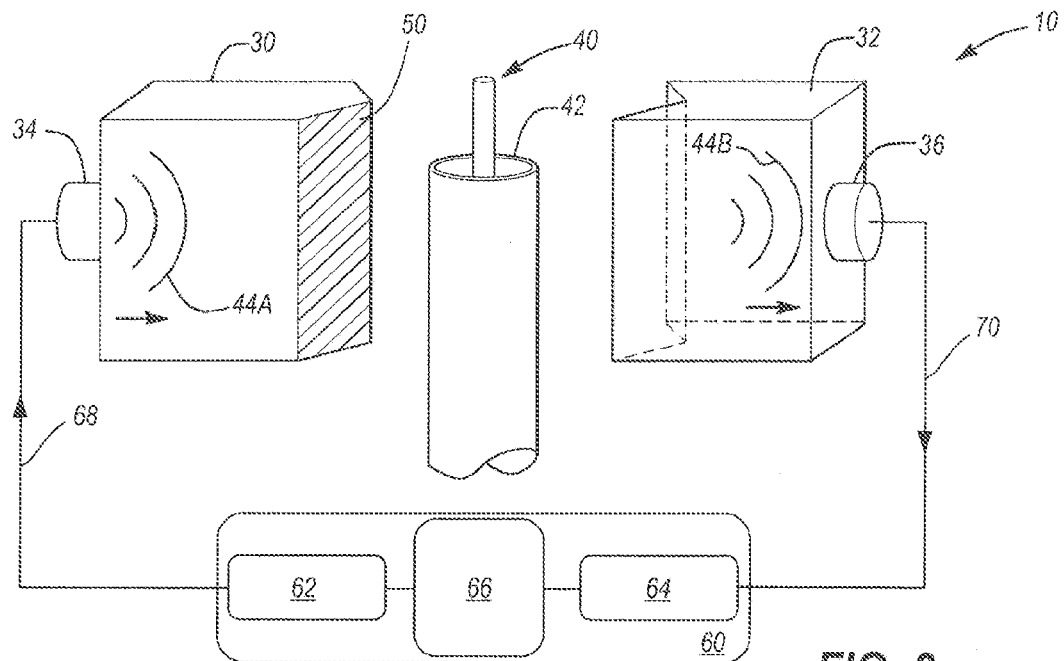
FIG. 3 is a schematic perspective view of a system that may be used to evaluate the quality of a wire crimp by examining the transmission of ultrasonic waves.

Referring to FIG. 3, the compression elements 30, 32 may be used to establish a mechanical engagement (i.e., a "crimp') between a wire 40 and a ferrule 42. For simplicity, the wire 40 is shown as a single strand wire; however multiple strands of wires may be bundled together as a cable without departing from the intended scope of the invention. As the compression elements 30, 32 are brought together (see FIG. 2) they may contact the ferrule on substantially opposing sides and deform/compress the ferrule 42 around the wire 40, thus forming a crimp that may provide both a mechanical and an electrical coupling between the wire 40 and ferrule 42. While only two compression elements are illustrated, additionally compression elements may be used. For example, the compression elements may be configured to operate in pairs that may be co-linearly mounted around the ferrule and wire axis. All of the included compression elements may be mechanically connected so that when the UECT is activated, all pairs advance toward the ferrule and wire axis.

When re-certifying an existing crimp, the compression elements 30, 32 may engage the wire 40/ferrule 42 with a large enough force to establish intimate contact with the crimp, however, with a small enough force to avoid causing additional plastic deformation in the ferrule. To aid in establishing secure, yet non-deforming contact, a contact-promoting material 50 may be disposed on the contact surface of the compression elements 30, 32 (i.e., on the portion of the compression elements 30, 32 that are configured to contact the ferrule 42). The contact-promoting material 50 may be a reusable material (e.g., a removable, pressure deforming adhesive) that may promote the transfer of ultrasonic energy between the compression elements 30, 32 and the wire 40/ferrule 42. In an embodiment, the contact material 50 may have an elastomeric base. Alternative contact materials may be used if they are moldable and known to conduct ultrasonic energy efficiently and/or consistently (i.e., where any loss or attenuation can be predictably modeled). It may also be preferable (though not necessary) for the contact material to possess a specific acoustic impedance similar to that of the compression elements 30, 32 to minimize any ultrasonic refractions/reflections (and hence energy loss) to reflections at the interfaces between the couplant and the compression elements (jaws).

An ultrasonic transducer 34, 36 may be coupled with each respective compression element 30, 32 in a manner that allows an ultrasonic signal to freely pass between the transducer and the respectively coupled compression element. Each transducer 34, 36 may be capable of generating an ultrasonic acoustic wave from a received electrical signal, or vice versa. As schematically illustrated in FIG. 3, in an embodiment, the first ultrasonic transducer 34 (i.e., the transmitting transducer 34) may be configured to transmit an ultrasonic signal 44A to the first compression element 30 in response to a received analog electrical signal 68. The signal 44A may then be transmitted from the compression element 30 to the ferrule-wire complex (e.g. to ferrule 42 through wire 40 and through ferrule 42). Subsequently, the ultrasonic signal 44B may pass from wire 40 and ferrule 42 to the second compression element 32, where it may be received by the second ultrasonic transducer 36 (i.e., the receiving transducer 36) and converted into a second corresponding analog electrical signal 70. Such a configuration is commonly referred to as a "pitch-catch" ultrasonic arrangement. If multiple compression elements are used, one compression element may be configured as an ultrasonic transmitter, while the remainder of the compression elements may be configured as ultrasonic receiving transducers. In the remaining discussion one transmitter will be paired with one receiver, with the understanding that the output from one or more transmitter transducers may be received simultaneously by a number of receiving transducers.

As the signal passes through the ferrule 42 and wire 40, the quality of the crimp may alter various signal properties of the initially transmitted ultrasonic signal 44A. This may potentially result in a modified signal 44B being passed onto the second compression element 32. While the passed signal 44B may be substantially similar to the transmitted signal 44A, the passed signal 44B may be attenuated, phase shifted, and/or include various signal artifacts as a result of the crimp. By analyzing the ultrasonic signal passage (e.g., the signal differences between the ultrasonic signals 44B, 44A), the system may estimate the quality of the crimp (i.e., the deformation-caused forces between the wire surface and the ferrule surface, which affect asperity density at the wire 40/ferrule 42 interface).

As schematically illustrated in FIG. 3, a signal processor 60 may be electrically coupled with each of the ultrasonic transducers 34, 36, and may include a signal transmitting module 62, a signal receiving module 64, and a signal analysis module 66. Each module 62, 64, 66 may employ the use of hardware and/or software, and may include one or more microprocessors or central processing units (CPU), read only memory (ROM), random access memory (RAM), electrically-erasable programmable read only memory (EEPROM), a high-speed clock, analog-to-digital (A/D) circuitry, digital-to-analog (D/A) circuitry, and any required input/output (I/O) circuitry and devices, as well as signal conditioning and buffering electronics.

In an embodiment, for example, the transmitting module 62 may include any power electronic components that may be necessary to provide the transmitting transducer 34 with an analog electrical signal 68 that may cause the transmitting transducer 34 to generate an ultrasonic acoustic wave 44A with one or more frequency components falling within the ultrasonic frequency range. As may be understood, this range may be defined as approximately 200 KHz to approximately 1000 MHz, however, it may more generally be characterized by the range of ultrasonic frequencies above the human audible frequency range.

The receiving module 64 may include any input circuitry that may be necessary to receive, sample, and/or digitize an analog electrical signal 70 provided by the receiving transducer 36 in response to a received ultrasonic signal 44B. For example, the receiving module 64 may include amplification circuitry, signal filters, A/D converters, sample and hold circuitry, and/or calibration circuitry. The receiving module 64, for example, may output a digital representation of the received analog electrical signal 70

Finally, the signal analysis module 66 may be configured to analyze the digital representation of the analog electrical signal 70 received by the receiving module 64 with respect to the timing and other characteristics of electrical signal 68 transmitted by the transmitting module 62 to locate and identify physical origins of significant patterns in electrical signals 70. The signal analysis module 66 may operate in either the time domain, or in the frequency domain, and may be capable of performing one or more Fourier transforms, fast Fourier transforms, discrete Fourier transforms, Hilbert transforms, or other similar operations. In an embodiment, the signal analysis module 66 may include, for example, a processor (e.g., a digital signal processor (DSP)), I/O circuitry, and volatile/non-volatile memory.

While the signal processor 60 is schematically illustrated as a single device for simplicity and clarity, elements of the processor 60 may be distributed over as many different hardware and software components as are required. The individual control routines/systems resident in the processor 60 or readily accessible thereby may be stored in ROM or other suitable tangible memory location and/or memory device, and automatically executed by associated hardware components of the processor 60 to provide the respective control and analysis functionality.

As generally explained above, during the initial crimping process, the deformation of the ferrule 42 with respect to the wire(s) 40 creates a number of points of contact between the asperities of the wire(s) and the asperities of the ferrule. The asperity contact points enable ultrasonic transmission across the wire 40 and the ferrule 42, and therefore between the transmitting transducer 34 to the receiving transducer 36. Changes in the crimp quality, such as through corrosion or relaxation of the crimp/ferrule may reduce the density of the asperity contacts, thus resulting in a modified and/or degraded ultrasonic transmission. The signal analysis module 66 is, therefore, configured to examine the ultrasonic transmission through the wire 40/ferrule 42 interface to deduce the density of the asperity contact points, and thus the electrical conductivity of the crimp.

Figure 4:
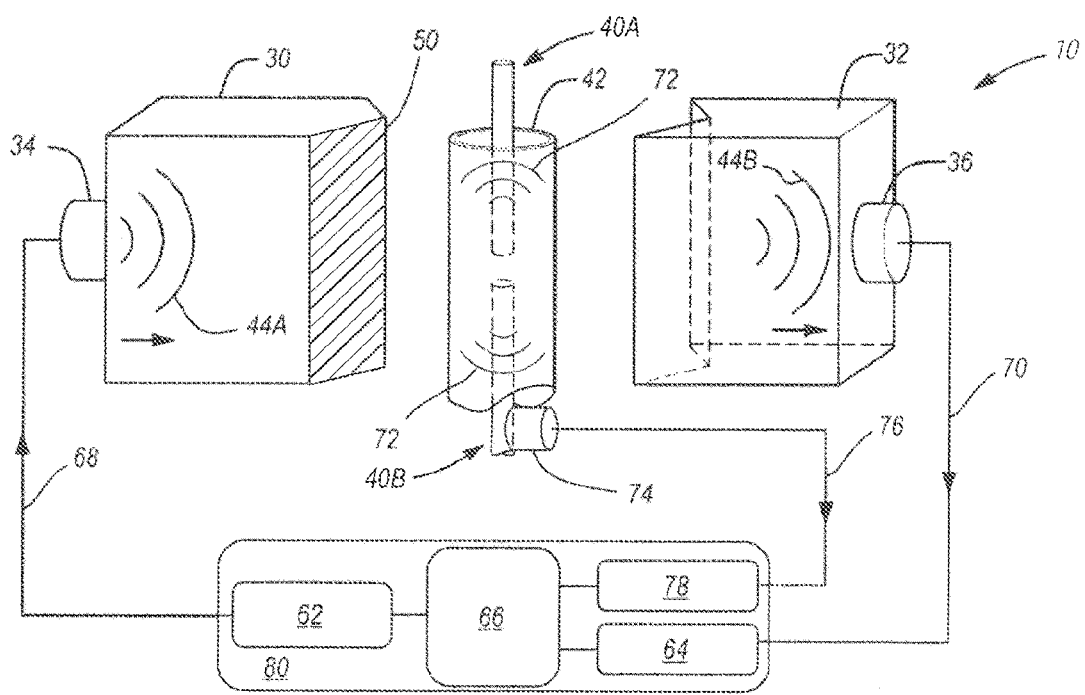
FIG. 4 is a schematic perspective view of a system that may be used to evaluate the quality of a wire crimp by examining the transmission of ultrasonic waves.

In FIG. 3, the system 10 is configured to analyze an ultrasonic wave (e.g., 44A and 44B) that is radially passed through the wire 40 and ferrule 42. In FIG. 4, the system is additionally configured to analyze a shear or other mode-converted ultrasonic wave 72 that may axially translate down the wire 40. As may be understood, this ultrasonic wave 72 may be a resultant wave caused by the radial injection of the compressional or other ultrasonic wave. Accordingly, the signal properties of the ultrasonic wave 72 may relate to the signal properties of the transmitted ultrasonic wave 44A. The received ultrasonic wave 44B may be used to analyze and/or characterize the quality of the crimp formation, while the received waves 72 may, for example, be used to analyze and/or characterize the degree of corrosion at the crimp.

As illustrated in FIG. 4, an ultrasonic transducer 74 may be placed in contact with joined wires 40A and 40B to detect the transmission of the ultrasonic wave 72 along the axial dimension of wire 40B. For example, the ultrasonic transducer 74 may be configured to detect any radial motion of the wire for the presence of a mode-shifted wave 72 which may propagate through the wire 40B. The ultrasonic transducer 74 may convert any sensed ultrasonic vibration into a corresponding analog electrical signal 76 that may be received by the signal processor 80 via a second receiving module 78. Signal processor 80 may be substantially similar to signal processor 60, with the exception of the second included receiving module 78.

In an embodiment, the ultrasonic transducer 74 may be ultrasonically coupled with the wire 40, itself, such as at a bare/stripped portion of the wire 40 near the ferrule 42. In another embodiment, the ultrasonic transducer 74 may be ultrasonically coupled with the wire insulation (not shown), assuming the insulation conducts the ultrasonic waves from the wire 40B.

Figure 5:
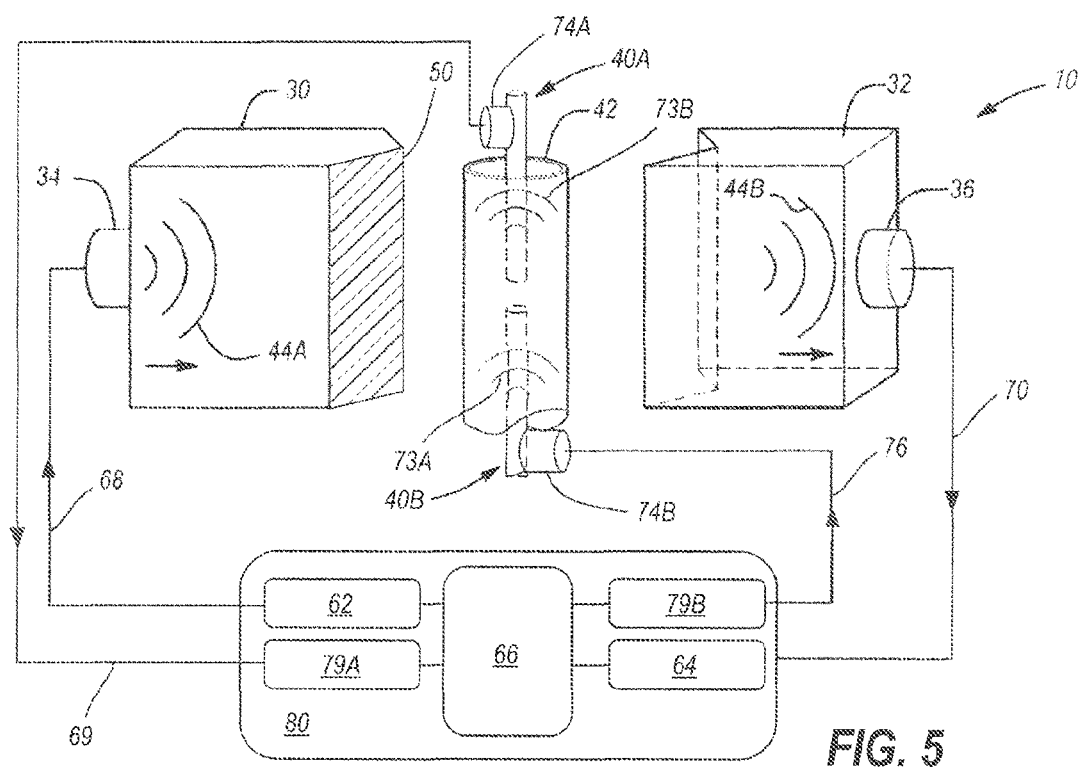
FIG. 5 is a schematic perspective view of a system that may be used to evaluate the quality of a wire crimp by examining the transmission of ultrasonic waves.

FIG. 5 illustrates a variation of the system 10, where a first ultrasonic transducer 74A is disposed on wire 40A, and a second ultrasonic transducer 74B is disposed on wire 40B. Modules 79A and 79B may be similar to receiving module 78 provided in FIG. 4, with the exception that they may both transmit and receive ultrasonic signals. For example, as shown, module 79B may transmit an analog electrical signal 76 to an ultrasonic transducer 74B where it may be converted into an ultrasonic wave 73A. This wave may be transmitted through the wire-ferrule-wire complex 40B, 42, 40A, and received by ultrasonic transducer 74A, where it may be converted again into an analog electrical signal 69. Module 79A may then be configured to receive the analog electrical signal 69, and communicate it to the signal analysis module 66. Such a configuration may allow the wire-mounted transducers 74A, 74B to analyze a separate dimension of the ferrule-complex than the transducers 34, 36.

Figure 6:
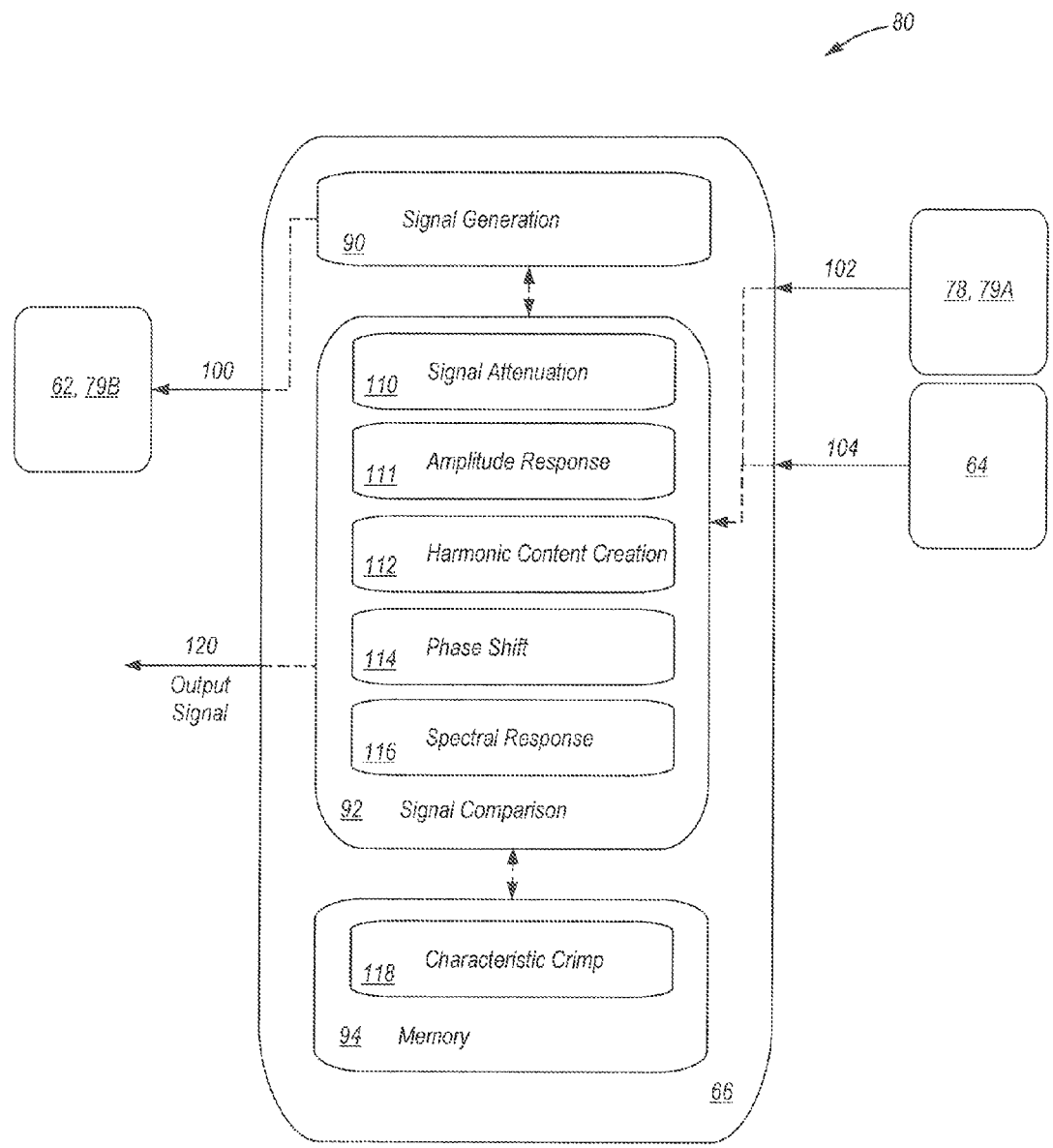
FIG. 6 is a schematic diagram of the signal processor represented in FIGS. 4 and 5.

FIG. 6 is a schematic diagram of the signal processor 80, with further clarity provided into the function/structure of the signal analysis module 66. As shown, the signal analysis module 66 may include a signal generation sub-module 90, a signal comparison sub-module 92, and memory 94. As may be appreciated, each module 62, 64, 66, 78 and/or sub-module 90, 92 may be embodied by hardware and/or software, and may be provided within a single multi-purpose processor, or distributed over various components.

In general, the signal generation sub-module 90 may determine the parameters and/or composition of the desired electrical output signal 68, and may command the transmitting module 62 to produce such a signal. For example, the signal generation sub-module 90 may provide the transmitting module 62 with a transmit signal 100 that identifies one or more component frequencies, each having a respective amplitude. The transmitting module 62 may then generate and transmit the analog electrical signal 68 to the ultrasonic transducer 34, based on the various identified frequencies/amplitudes.

The signal comparison sub-module 92 may receive a digital representation of any sensed waves 72 and/or any sensed waves 44B from the respective receiving modules 78, 64 via the respective signal 102 and 104. The signal comparison sub-module 92 may further be in communication with the signal generation sub-module 90, and may receive an indication of the nature of the commanded output signal 68.

Using a variety of analysis methods, the signal comparison sub-module 92 may compare the signal parameters of the sensed waves 44B, 72, 73B with the commanded parameters of the transmitted waves 44A to make an assessment of the quality of the crimp. More specifically, the signal comparison sub-module 92 may examine the received signals 102, 104 relative to the transmit signal 100 for evidence of signal differences that may be specifically attributable to the crimp, such as signal amplitude attenuation 110, amplitude response 111 harmonic content creation 112, phase shifts 114, and/or changes in the spectral resonance and/or interference patterns 116.

In an embodiment, the signal comparison sub-module 92 may compare any signal differences identified through the various analysis techniques 110, 111, 112, 114, 116 to similar "baseline" parameters that may be representative of a "characteristic" or "ideal" crimp. These "baseline" characteristic crimp parameters 118 may be stored in a memory device 94 that may be accessible by the signal comparison sub-module 92. The baseline characteristic crimp parameters 118 may, for example, be averages that are empirically determined from a statistical sample of ideal crimps that have a similar wire and ferrule gauge, thickness, and material composition. Alternatively, during a re-certification analysis, the "characteristic crimp" parameters 118 may be the actual recorded test data of the crimp-in-question from a previous analysis. For example, a crimp may be ultrasonically analyzed during installation, at which time the signal parameters from an ultrasonic test may be recorded in memory 94. During a re-certification analysis, the installation parameters 118 of the in-service crimp may be recalled, such as through a serial number look-up, and then compared to the signal parameters determined by the signal comparison sub-module 92. Such a comparison may be used to determine any crimp degradation that may have occurred along the crimp's in-service life.

When the signal analysis module 66 examines the signal attenuation 110 caused by a crimp, it may first command the transmitting module 62 to generate an analog electrical signal 68 having a particular frequency, phase, and amplitude (i.e., via the signal generation sub-module 90). The signal comparison module 66 may then examine the received signals 102, 104 with respect to signal parameters of the transmitted signal 100 to determine how much the crimp attenuates the amplitude of the transmitted signal 100. As may be appreciated, some attenuation may be attributable to the materials and transducers, however, the processor 60 may account for such predictable attenuation in its analysis/comparison. In one embodiment, identification of the attenuation may be performed at a single frequency, which may be chosen due to particular characteristics of the crimp. In another embodiment, the identification may be performed at multiple frequencies, such as with a single frequency sweep, or with a composite signal having multiple frequency components. In a multiple frequency analysis, the signal analysis module 66 may assemble a bode plot to characterize the signal amplitude attenuation and/or to compare with a similar bode plot representative of a characteristic "good" crimp 118.

When analyzing the harmonic content creation 112, the signal analysis module 66 may command the transmitting module 62 to generate an analog electrical signal 68 having a single frequency, or a narrow band around a single frequency and a range of amplitudes. The spectral components of the received signals 100, 102 may be analyzed for any evidence of frequency content that may be induced via the crimp at frequencies different from the transmitted frequency. Similarly, the spectral components of the received signals 100, 102 may be analyzed for any evidence of amplitude-dependent frequency content that may be induced via the crimp at frequencies different from the transmitted frequency. Such an analysis may, for example, detect loose wire 40/ferrule 42 connections, where the wire 40 may reverberate against the ferrule 42 at frequency multiples of the transmitted ultrasonic 44A frequency. Another cause of a poor connection may be where the ferrule was not properly heat treated, and therefore does not have sufficient strength to avoid relaxing over time. Still another cause of a poor connection may be where the ferrule formed cracks during formation or during service life, or relaxed due to material dimensional change during service life, and therefore does not have sufficient strength to preserve intimate contact between the wire and the ferrule over time.

In an embodiment, when analyzing the harmonic content creation 112 as a function of amplitude 111, the signal generation sub-module 90 may sweep the frequency of the transmit signal 100 over a range of frequencies and amplitudes. The signal comparison sub-module 92 may then continuously analyze the received signals 102, 104, for evidence of modulations in spectral energy throughout the sweep. This swept frequency technique may aid in identifying crimp degradation that is only responsive to select frequencies within the range.

While the signal attenuation and harmonic content creation analyses 110, 111, 112 may primarily examine the amplitude of the received signals 102, 104, the signal analysis module 66 may also analyze the amount of phase shift 114 of the received signals 102, 104 with respect to the transmitted signal 100. Furthermore, while sweeping the frequency of the transmit signal 100 across a range of frequencies, the signal analysis module 66 may also look for the existence of constructive or destructive resonance 116, and may identify the frequencies at which such resonance occurs.

With each analysis technique described above (e.g., techniques 110, 111, 112, 114, and 116), the signal analysis module 66 may either view the results in a stand-alone context, or with respect to the parameters of the baseline characteristic crimp 118 stored in memory 94. For example, evidence of induced harmonic content 112 or amplitude-dependent induced harmonic content 111, 112 may be viewed in isolation (i.e., against a baseline of zero induced content), and therefore, may be interpreted as a sign of crimp degradation. Conversely, resonant frequencies and interference patterns may be compared to a previously-recorded baseline or a statistically-derived baseline to determine whether the resonant frequency and/or interference pattern has shifted away from an expected norm (i.e., the magnitude of a frequency shift may be more significant than the frequency itself). Similarly, while some degree of signal attenuation 110 may be expected, however a large deviation from a baseline may indicate crimp degradation.

In an embodiment, other wave-modes may be generated by the signal transmitting module 62 or within the crimp itself to examine the quality of the crimp. For example, surface and/or bulk waves may be generated/analyzed to examine the areal concentration of asperities between the wire 40 and ferrule 42. Additionally, signal analysis module 66 may examine changes in the polarization of the transmitted wave to, for example, determine and/or characterize the asperity pattern.

As may be appreciated, temperature of the crimp and/or the pressure applied to the crimp may also affect the analysis results. Therefore, the test data may be further correlated to the temperature and or applied pressure conditions during the test. In particular, the temperature of the crimp may be measured via a thermocouple or via infrared thermometry technologies and sensors associated with the compression elements 30, 32. Additionally, the temperature of the crimp may be controlled, such as by using an external heating element, to create a testing temperature profile similar to the in-service temperature profile that the crimp is expected to experience. Likewise, the pressure applied by the compression elements 30, 32 may be controlled to avoid introducing any additional plastic strain to the crimp (i.e., pressure may be maintained within the elastic strain range of the ferrule 42).

Alternatively, the temperature of the crimp may be varied during the test to analyze the effects of temperature change on the crimp quality. For example, the ultrasonic wave 44 may be maintained in a pulsed phase locked loop, where the frequency or phase of the transmit signal 100 may be variable to maintain the phase-lock. The temperature of the crimp and/or pressure applied to the crimp may then be controllably varied while transmit frequency changes and/or phase changes are examined.

In another embodiment, an electrically neutral gas may be diffused into the crimp joint to alter the ultrasonic signal propagation through the crimp during the test. The diffusion/adsorption of an electrically neutral gas into the joint may, for example, alter the signals used in the ultrasonic detection thus enabling possible corrosion-related defects to be identified. Following the test, any residual gas that may be trapped within the joint could be driven off thermally and/or analyzed for asperity concentration. Different gasses can be chosen for their abilities to reduce oxidized states around asperities, and hence their ability to differentially affect ultrasonic conduction across the ferrule-wire complex.

The above listing of analysis techniques should be viewed as illustrative of techniques that may be employed, though should not in any way limit the scope of the invention. They each demonstrate that a crimp may have a particular "fingerprint" that may change over time (i.e., with the "fingerprint" being an analogy for how the crimp affects various parameters of an introduced ultrasonic signal). By analyzing the type and magnitude of the changes in the transmitted ultrasonic signal 44B, the signal analysis module 66 may draw conclusions about the quality of the crimp.

If the crimp examined by the system 10 has substantially changed from the stored baseline characteristic crimp 118, the signal analysis module 66 may then alert a user to impending off-normal electrical performance, such as by providing an output signal 120 to a display device. For example, the output signal 120 may visually convey the differences to a visual display or oscilloscope, or may indicate a "fail" condition via an indicator light-emitting diode (LED) or audible alert. Similarly, if the crimp is within an acceptable range of the stored baseline characteristic crimp 118, the output signal may reflect a "pass" condition via the same output signal 120.

While some embodiments of the invention have been herein illustrated, shown and described, it is to be appreciated that various changes, rearrangements and modifications may be made therein, without departing from the scope of the invention as defined by the appended claims. It is intended that the specific embodiments and configurations are disclosed for practicing the invention, and should not be interpreted as limitations on the scope of the invention as defined by the appended claims and it is to be appreciated that various changes, rearrangements and modifications may be made therein, without departing from the scope of the invention as defined by the appended claims.

The invention claimed is:

1. A system for determining the quality of an electrical wire crimp between a wire and a ferrule, the system comprising:
   an ultrasonically equipped crimp tool (UECT) configured to transmit an ultrasonic acoustic wave through a wire and ferrule, the UECT including:
      a first ultrasonic transducer configured to generate an ultrasonic acoustic wave in response to a first analog electrical signal; and
      a second ultrasonic transducer configured to oppose the first ultrasonic transducer and configured to generate a second analog electrical signal in response to a sensed ultrasonic acoustic wave;
   a signal processor in communication with the UECT and with each of the respective first and second ultrasonic transducers, the signal processor including:
      a signal transmitting module configured to transmit the first analog electrical signal to the first ultrasonic transducer, the first analog electrical signal having a frequency within the ultrasonic frequency range;
      a signal receiving module configured to receive the second analog electrical signal from the second ultrasonic transducer; and
      a signal analysis module configured to identify signal differences between the first and second analog electrical signals that are attributable to the wire crimp, to compare the signal differences attributable to the wire crimp to a baseline, and to provide an output signal if the signal differences deviate from the baseline.

2. The system of claim 1, wherein the signal differences identified by the signal analysis module include an attenuation of the signal amplitude of the second analog electrical signal relative to the first analog electrical signal.

3. The system of claim 1, wherein the signal differences identified by the signal analysis module include a shift of the phase of the second analog electrical signal relative to the first analog electrical signal.

4. The system of claim 1, wherein the signal differences identified by the signal analysis module include a harmonic content within the second analog electrical signal at a multiple of the frequency of the first analog electrical signal.

5. The system of claim 1, wherein the signal processor is configured to sweep the frequency of the first electrical signal over a range of frequencies.

6. The system of claim 5, wherein the signal differences identified by the signal analysis module include resonance at a resonant frequency.

7. The system of claim 1, wherein the signal processor further includes non-volatile memory, and wherein the baseline includes a value stored in the non-volatile memory.

8. The system of claim 1, wherein the baseline is representative of the signal differences expected from a characteristic crimp, and wherein the characteristic crimp is a statistical average of a sample of crimps.

9. The system of claim 1, wherein the baseline is obtained by testing the electrical wire crimp during a previous test.

10. The system of claim 1, wherein the UECT includes a first compression element and a second compression element configured to contact the ferrule on substantially opposing sides of the ferrule, and wherein the first transducer is coupled with the first compression element, and wherein the second transducer is coupled with the second compression element.

11. The system of claim 10, wherein each of the first and second compression elements includes a contact-promoting material disposed on a portion of the respective element that is configured to contact the ferrule, the contact-promoting material having an adhesive quality.

12. The system of claim 1, further comprising a third ultrasonic transducer in communication with the wire and configured to generate a third analog electrical signal in response to a sensed shear ultrasonic acoustic wave;
wherein the signal processor further includes a second signal receiving module configured to receive the third analog electrical signal from the third ultrasonic transducer; and
wherein the signal analysis module is further configured to identify signal differences between the first and third analog electrical signals that are attributable to the wire crimp.

13. A system for determining the quality of an electrical wire crimp between a wire and a ferrule, the system comprising:
an ultrasonically equipped crimp tool (UECT) configured to transmit an ultrasonic acoustic wave through a wire and ferrule, the UECT including:
a first ultrasonic transducer configured to generate an ultrasonic acoustic wave in response to a first analog electrical signal; and
a second ultrasonic transducer configured to oppose the first ultrasonic transducer and configured to generate a second analog electrical signal in response to a sensed ultrasonic acoustic wave;
a third ultrasonic transducer in communication with the wire and configured to generate a third analog electrical signal in response to a sensed shear ultrasonic acoustic wave;
a signal processor in communication with the UECT and with each of the respective first and second ultrasonic transducers, the signal processor including:
a signal transmitting module configured to transmit the first analog electrical signal to the first ultrasonic transducer, the first analog electrical signal having a frequency within the ultrasonic frequency range;
a first signal receiving module configured to receive the second analog electrical signal from the second ultrasonic transducer;
a second signal receiving module configured to receive the third analog electrical signal from the third ultrasonic transducer; and
a signal analysis module configured to identify signal differences between the first and second analog electrical signals and between the first and third analog electrical signals that are attributable to the wire crimp, to compare the signal differences attributable to the wire crimp to a baseline, and to provide an output signal if the signal differences deviate from the baseline.

14. The system of claim 13, wherein the signal differences identified by the signal analysis module include an attenuation of the signal amplitude of the second analog electrical signal relative to the first analog electrical signal.

15. The system of claim 13, wherein the signal differences identified by the signal analysis module include a shift of the phase of the second analog electrical signal relative to the first analog electrical signal.

16. The system of claim 13, wherein the signal differences identified by the signal analysis module include a harmonic content within the second analog electrical signal at a multiple of the frequency of the first analog electrical signal.

17. The system of claim 13, wherein the signal processor further includes non-volatile memory, and wherein the baseline includes a value stored in the non-volatile memory.

18. The system of claim 13, wherein the baseline is representative of the signal differences expected from a characteristic crimp, and wherein the characteristic crimp is a statistical average of a sample of crimps.

19. The system of claim 13, wherein the baseline is obtained by testing the electrical wire crimp during a previous test.

* * * * *